(12) United States Patent
Bobgan et al.

(10) Patent No.: US 10,327,344 B2
(45) Date of Patent: Jun. 18, 2019

(54) MEDICAL DEVICE HOUSING WITH WELD JOINT FEATURES

(71) Applicant: Cardiac Pacemakers, Inc., St. Paul, MN (US)

(72) Inventors: Jean M. Bobgan, Maple Grove, MN (US); David P. Stieper, North Branch, MN (US); Mark A. Lamberty, Cottage Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/488,908

(22) Filed: Apr. 17, 2017

(65) Prior Publication Data

US 2017/0303411 A1   Oct. 19, 2017

Related U.S. Application Data

(60) Provisional application No. 62/324,219, filed on Apr. 18, 2016.

(51) Int. Cl.
*G16H 40/67* (2018.01)
*H05K 5/02* (2006.01)
(Continued)

(52) U.S. Cl.
CPC ......... *H05K 5/0217* (2013.01); *A61B 5/0022* (2013.01); *A61B 5/0031* (2013.01); *A61B 5/0205* (2013.01); *A61B 5/0215* (2013.01); *A61B 5/02444* (2013.01); *A61B 5/686* (2013.01); *A61N 1/375* (2013.01); *G16H 40/67* (2018.01); *A61B 5/11* (2013.01); *A61N 1/3655* (2013.01); *A61N 1/36521* (2013.01); *A61N 1/36535* (2013.01); *A61N 1/36542* (2013.01); *A61N 1/36564* (2013.01); *A61N 1/36578* (2013.01); *A61N 1/3754* (2013.01); *A61N 1/3756* (2013.01); *A61N 1/3758* (2013.01);
(Continued)

(58) Field of Classification Search
CPC .................................................. H05K 5/0217
USPC ........................................................ 174/504
See application file for complete search history.

(56) References Cited

U.S. PATENT DOCUMENTS 5,173,841 A    12/1992   Uenaka et al.
5,481,434 A    1/1996    Banakis et al.
(Continued)

FOREIGN PATENT DOCUMENTS

WO    1995034342 A1    1/1996
WO    2002032503 A1    4/2002
WO    WO 02/32503    *   4/2002    ............. A61N 1/375

OTHER PUBLICATIONS

International Search Report and Written Opinion issued in PCT/US2017/027895, dated Oct. 10, 2017, 10 pages.
(Continued)

*Primary Examiner* — Stanley Tso

(57) ABSTRACT

Aspects of the present disclosure are directed toward a medical device having a a core assembly. The core assembly includes a core circuit assembly and a core assembly housing configured to enclose the core circuit assembly. The core assembly housing includes a first portion, and a second portion configured to be coupled to the first portion along a weld seam. The second portion includes at least one weld joint feature, which includes a thinned section of the second portion.

11 Claims, 6 Drawing Sheets

(51) Int. Cl.

| | | |
|---|---|---|
| *A61N 1/375* | (2006.01) | |
| *A61B 5/00* | (2006.01) | |
| *A61B 5/0205* | (2006.01) | |
| *A61B 5/0215* | (2006.01) | |
| *A61B 5/024* | (2006.01) | |
| *A61N 1/39* | (2006.01) | |
| *A61N 1/365* | (2006.01) | |
| *A61B 5/11* | (2006.01) | |

(52) U.S. Cl.
CPC ........ *A61N 1/37512* (2017.08); *A61N 1/3968* (2013.01); *A61N 1/39622* (2017.08)

(56) References Cited

U.S. PATENT DOCUMENTS

| | | |
|---|---|---|
| 5,851,221 A | 12/1998 | Rieder et al. |
| 5,871,514 A | 2/1999 | Wiklund et al. |
| 6,552,911 B1 * | 4/2003 | Haupt .................... B23K 26/28 174/50 |
| 6,658,296 B1 | 12/2003 | Wong et al. |
| 7,236,834 B2 | 6/2007 | Christopherson et al. |
| 7,288,736 B2 * | 10/2007 | Schildgen .............. A61N 1/375 219/121.63 |
| 7,349,216 B2 | 3/2008 | Silverbrook et al. |
| 7,414,855 B1 | 8/2008 | Arnold |
| 7,544,220 B2 | 6/2009 | Zhao et al. |
| 8,093,991 B2 | 1/2012 | Stevenson et al. |
| 2003/0204216 A1 | 10/2003 | Ries et al. |
| 2006/0217778 A1 | 9/2006 | Strom et al. |
| 2007/0016089 A1 | 1/2007 | Fischell et al. |
| 2008/0303728 A1 | 12/2008 | Lee et al. |
| 2009/0124965 A1 | 5/2009 | Greenberg et al. |
| 2010/0089634 A1 * | 4/2010 | Ahn ..................... H02G 3/0418 174/504 |
| 2012/0203314 A1 | 8/2012 | Deininger et al. |
| 2014/0133123 A1 | 5/2014 | Prasannakumar et al. |
| 2015/0157862 A1 | 6/2015 | Greenberg et al. |
| 2016/0061760 A1 * | 3/2016 | Nagel .................. G01N 27/025 324/654 |
| 2017/0157405 A1 | 6/2017 | Deininger et al. |

OTHER PUBLICATIONS

International Search Report and Written Opinion issued in PCT/US2017/028010, dated Oct. 9, 2017, 12 pages.

* cited by examiner

MEDICAL DEVICE HOUSING WITH WELD JOINT FEATURES

CROSS-REFERENCE TO RELATED APPLICATION

This application claims priority to Provisional Application No. 62/324,219, filed Apr. 18, 2016, which is herein incorporated by reference in its entirety.

TECHNICAL FIELD

Embodiments of the present disclosure relate to medical devices and systems for sensing physiological parameters and/or delivering therapy. More specifically, embodiments of the disclosure relate to casings of implantable medical devices.

BACKGROUND

Implantable medical devices (IMDs) may be configured to sense physiological parameters and/or provide therapy and may include one or more electrodes for performing aspects of these functions. The overall usable volume enclosed within a housing of an IMD may be adjusted based on considerations of patient comfort and performance.

SUMMARY

Embodiments of the disclosure include an implantable medical device having a housing designed to increase internal volume and allow for welding of two portions thereof together without using a separate weld ring.

In an Example 1, a medical device comprises a core circuitry assembly; and a core assembly housing configured to enclose the core circuitry assembly, the core assembly housing comprising: a first portion; and a second portion configured to be coupled to the first portion along a weld seam, the second portion comprising at least one weld joint feature, wherein the at least one weld joint feature includes a thinned section of the second portion.

In an Example 2, the medical device of Example 1, wherein the at least one weld joint feature comprises at least one of a flange and a wedge-shaped edge of at least one wall of the second portion.

In an Example 3, the medical device of either of Examples 1 and 2, the first portion comprising: a first side wall; a first lower wall coupled to the first side wall by a first curved corner portion and extending in a direction away from an inside surface of the first side wall; and a first upper wall coupled to the first side wall by a second curved corner portion and extending in a direction away from the inside surface of the first side wall; and the second portion comprising: a second side wall; a second lower wall coupled to the second side wall by a third curved corner portion and extending in a direction away from an inside surface of the second side wall; and a second upper wall coupled to the side wall by a second curved corner portion and extending in a direction away from an inside surface of the second side wall.

In an Example 4, the medical device of Example 3, wherein the at least one weld joint feature includes a first flange that is recessed with respect to an outside surface of the second lower wall and a second flange that is recessed with respect to an outside surface of the second upper wall.

In an Example 5, the medical device of Example 4, the at least one weld joint feature further comprising a third flange that is recessed with respect to an inside surface of the first lower wall and a fourth flange that is recessed with respect to an inside surface of the first upper wall.

In an Example 6, the medical device of either of Examples 4 or 5, wherein the first and second flanges act as an integrated weld ring to protect the core circuitry assembly from the energy applied during a welding procedure.

In an Example 7, the medical device of Example 3, wherein the at least one weld joint feature includes a wedge-shaped section of an outside surface of the second lower wall and a wedge-shaped section of an outside surface of the second upper wall.

In an Example 8, the medical device of Example 7, wherein the at least one weld joint feature further includes a wedge-shaped section of an inside surface of the first lower wall and a wedge-shaped section of an inside surface of the first upper wall.

In an Example 9, the medical device of either of Examples 7 or 8, wherein the wedge-shaped section of the outside surface of the second lower wall and the wedge-shaped section of the outside surface of the second upper wall act as an integrated weld ring to protect the core circuitry assembly from the energy applied during a welding procedure.

In an Example 10, a medical device comprises: a core circuitry assembly; and a core assembly housing configured to enclose the core circuitry assembly, the core assembly housing comprising: a first portion comprising: (1) a first side wall; (2) a first lower wall coupled to the first side wall by a first curved corner portion and extending in a direction away from an inside surface of the first side wall; and (3) a first upper wall coupled to the first side wall by a second curved corner portion and extending in a direction away from the inside surface of the first side wall; a second portion configured to be coupled to the first portion along a weld seam, the second portion comprising: (1) a second side wall; (2) a second lower wall coupled to the second side wall by a third curved corner portion and extending in a direction away from an inside surface of the second side wall; and (3) a second upper wall coupled to the side wall by a second curved corner portion and extending in a direction away from an inside surface of the second side wall; and at least one weld joint feature, wherein the at least one weld joint feature includes a thinned section of the second portion.

In an Example 11, the medical device of Example 10, wherein the thinned section of the second portion comprises at least one of a flange and a wedge-shaped section.

In an Example 12, a method of manufacturing a medical device comprises: providing a core circuitry assembly; forming a first portion of a core assembly housing, the first portion comprising a first weld joint feature, wherein the first weld joint feature includes a thinned section of the first portion; forming a second portion of the core assembly housing, the second portion comprising a second weld joint feature, wherein the second weld joint feature includes a thinned section of the second portion; positioning the first and second portions around the core circuitry assembly such that the first weld joint feature is positioned adjacent to the second weld joint feature; and welding the first and second portions together along the first and second weld joint features.

In an Example 13, the method of Example 12, wherein the thinned section of the first portion comprises at least one of a flange and a wedge-shaped section of the first portion.

In an Example 14, the method of either of Examples 12 or 13, wherein the thinned section of the second portion comprises at least one of a flange and a wedge-shaped section of the second portion.

In an Example 15, the method of Example 13, wherein welding the first and second portions together comprises laser welding the first and second portions together.

In an Example 16, a medical device comprises: a core circuitry assembly; and a core assembly housing configured to enclose the core circuitry assembly, the core assembly housing comprising: a first portion; and a second portion configured to be coupled to the first portion along a weld seam, the second portion comprising at least one weld joint feature, wherein the at least one weld joint feature includes a thinned section of the second portion.

In an Example 17, the medical device of Example 16, wherein the at least one weld joint feature comprises at least one of a flange and a wedge-shaped edge of at least one wall of the second portion.

In an Example 18, the medical device of Example 16, the first portion comprising: a first side wall; a first lower wall coupled to the first side wall by a first curved corner portion and extending in a direction away from an inside surface of the first side wall; and a first upper wall coupled to the first side wall by a second curved corner portion and extending in a direction away from the inside surface of the first side wall; and the second portion comprising: a second side wall; a second lower wall coupled to the second side wall by a third curved corner portion and extending in a direction away from an inside surface of the second side wall; and a second upper wall coupled to the side wall by a second curved corner portion and extending in a direction away from an inside surface of the second side wall.

In an Example 19, the medical device of Example 18, wherein the at least one weld joint feature includes a first flange that is recessed with respect to an outside surface of the second lower wall and a second flange that is recessed with respect to an outside surface of the second upper wall.

In an Example 20, the medical device of Example 19, the at least one weld joint feature further comprising a third flange that is recessed with respect to an inside surface of the first lower wall and a fourth flange that is recessed with respect to an inside surface of the first upper wall.

In an Example 21, the medical device of Example 19, wherein the first and second flanges act as an integrated weld ring to protect the core circuitry assembly from the energy applied during a welding procedure.

In an Example 22, the medical device of Example 18, wherein the at least one weld joint feature includes a wedge-shaped section of an outside surface of the second lower wall and a wedge-shaped section of an outside surface of the second upper wall.

In an Example 23, the medical device of Example 22, wherein the at least one weld joint feature further includes a wedge-shaped section of an inside surface of the first lower wall and a wedge-shaped section of an inside surface of the first upper wall.

In an Example 24, the medical device of Example 22, wherein the wedge-shaped section of the outside surface of the second lower wall and the wedge-shaped section of the outside surface of the second upper wall act as an integrated weld ring to protect the core circuitry assembly from the energy applied during a welding procedure.

In an Example 25, a medical device comprises: a core circuitry assembly; and a core assembly housing configured to enclose the core circuitry assembly, the core assembly housing comprising: a first portion comprising: (1) a first side wall; (2) a first lower wall coupled to the first side wall by a first curved corner portion and extending in a direction away from an inside surface of the first side wall; and (3) a first upper wall coupled to the first side wall by a second curved corner portion and extending in a direction away from the inside surface of the first side wall; a second portion configured to be coupled to the first portion along a weld seam, the second portion comprising: (1) a second side wall; (2) a second lower wall coupled to the second side wall by a third curved corner portion and extending in a direction away from an inside surface of the second side wall; and (3) a second upper wall coupled to the side wall by a second curved corner portion and extending in a direction away from an inside surface of the second side wall; and at least one weld joint feature, wherein the at least one weld joint feature includes a thinned section of the second portion.

In an Example 26, the medical device of Example 25, wherein the at least one weld joint feature includes a first flange that is recessed with respect to an outside surface of the second lower wall and a second flange that is recessed with respect to an outside surface of the second upper wall.

In an Example 27, the medical device of Example 26, the at least one weld joint feature further comprising a third flange that is recessed with respect to an inside surface of the first lower wall and a fourth flange that is recessed with respect to an inside surface of the first upper wall.

In an Example 28, the medical device of Example 26, wherein the first and second flanges act as an integrated weld ring to protect the core circuitry assembly from the energy applied during a welding procedure.

In an Example 29, the medical device of Example 25, wherein the at least one weld joint feature includes a wedge-shaped section of an outside surface of the second lower wall and a wedge-shaped section of an outside surface of the second upper wall.

In an Example 30, the medical device of Example 29, wherein the at least one weld joint feature further includes a wedge-shaped section of an inside surface of the first lower wall and a wedge-shaped section of an inside surface of the first upper wall.

In an Example 31, the medical device of Example 29, wherein the wedge-shaped section of the outside surface of the second lower wall and the wedge-shaped section of the outside surface of the second upper wall act as an integrated weld ring to protect the core circuitry assembly from the energy applied during a welding procedure.

In an Example 32, a method of manufacturing a medical device comprises: providing a core circuitry assembly; forming a first portion of a core assembly housing, the first portion comprising a first weld joint feature, wherein the first weld joint feature includes a thinned section of the first portion; forming a second portion of the core assembly housing, the second portion comprising a second weld joint feature, wherein the second weld joint feature includes a thinned section of the second portion; positioning the first and second portions around the core circuitry assembly such that the first weld joint feature is positioned adjacent to the second weld joint feature; and welding the first and second portions together along the first and second weld joint features.

In an Example 33, the method of Example 32, wherein the thinned section of the first portion comprises at least one of a flange and a wedge-shaped section of the first portion.

In an Example 34, the method of Example 32, wherein the thinned section of the second portion comprises at least one of a flange and a wedge-shaped section of the second portion.

In an Example 35, the method of Example 32, wherein welding the first and second portions together comprises laser welding the first and second portions together.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
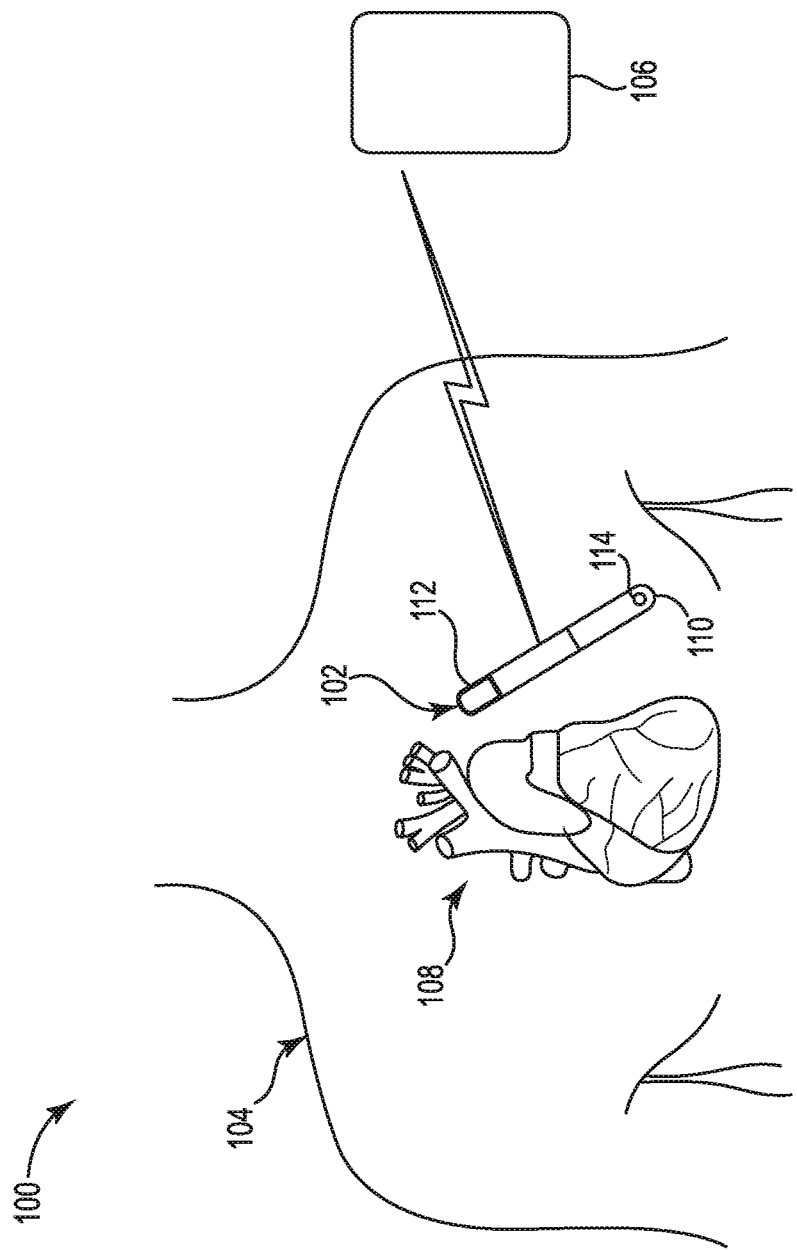
FIG. 1 is a schematic illustration depicting a patient monitoring system, in accordance with embodiments of the disclosure.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like. In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations.

For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient. In embodiments, however, the IMD 102 may include any type of IMD, any number of different components of an implantable system, and/or the like having a housing and being configured to be implanted in a patient's body 104. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the patient's body and/or the IMD 102. In various embodiments, the IMD 102 may include both defibrillation and pacing/CRT capabilities (e.g., a CRT-D device).

As shown, the IMD 102 may include a housing 110 having two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2A:
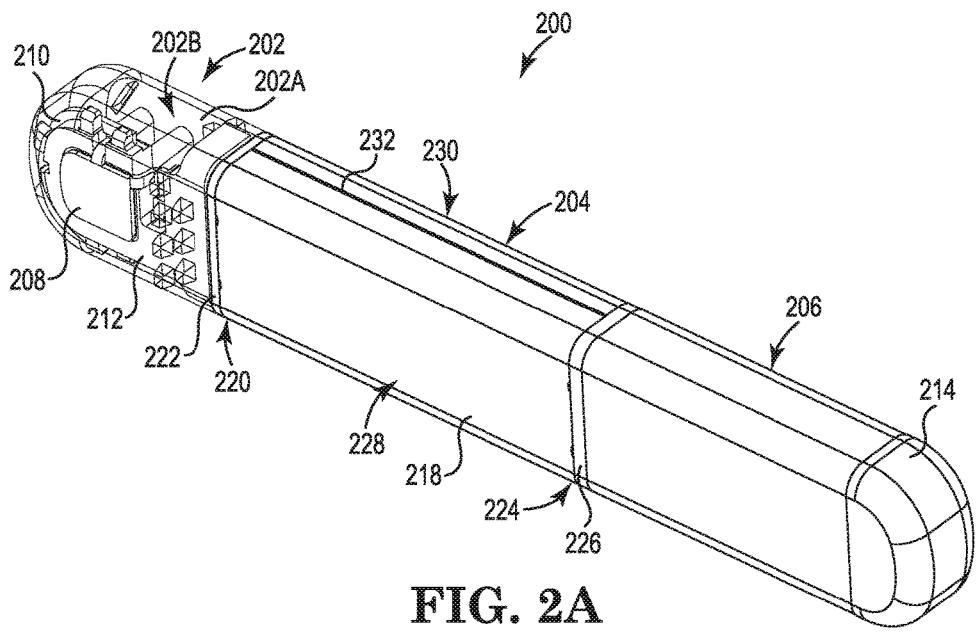
FIG. 2A is a perspective view of an implantable medical device (IMD), in accordance with embodiments of the disclosure.

FIG. 2A is a perspective view of an implantable medical device (IMD) 200, in accordance with embodiments of the disclosure. The IMD 200 may be, or may be similar to, the IMD 102 depicted in FIG. 1. As shown, the IMD 200 may include a header 202 arranged at or near a first end 220 of a core assembly 204. A battery assembly 206 (which may include one or more batteries) is arranged near a second end 224 of the core assembly 204. The header 202 includes a housing 202A that encloses an interior region 202B. The header 202 may house various circuitry components within its interior. The housing 202A may contact a patient's bodily tissue when the IMD 200 is subcutaneously implanted in an implantation location or pocket in the patient's chest or abdomen. The interior region 202B of the header 202 may house circuit components (e.g., an electrode 208 and an antenna 210) positioned and supported by a scaffold assembly 212. As shown, the IMD 200 may include, in addition to the electrode 208, an electrode 214 disposed at an end of the battery assembly 206. In embodiments, the electrode 214 may be integrated with the battery assembly 206, a housing of the battery assembly 206, and/or the like. In order to enable sensing of physiological parameters within the patient, the electrode 208 may be positioned to be flush with an interior surface of the housing 202A of the header 202. In other instances, the electrode 208 may be positioned by the scaffold assembly 212 to form a portion of an exterior surface of the housing 202A of the header 202.

Figure 2B:
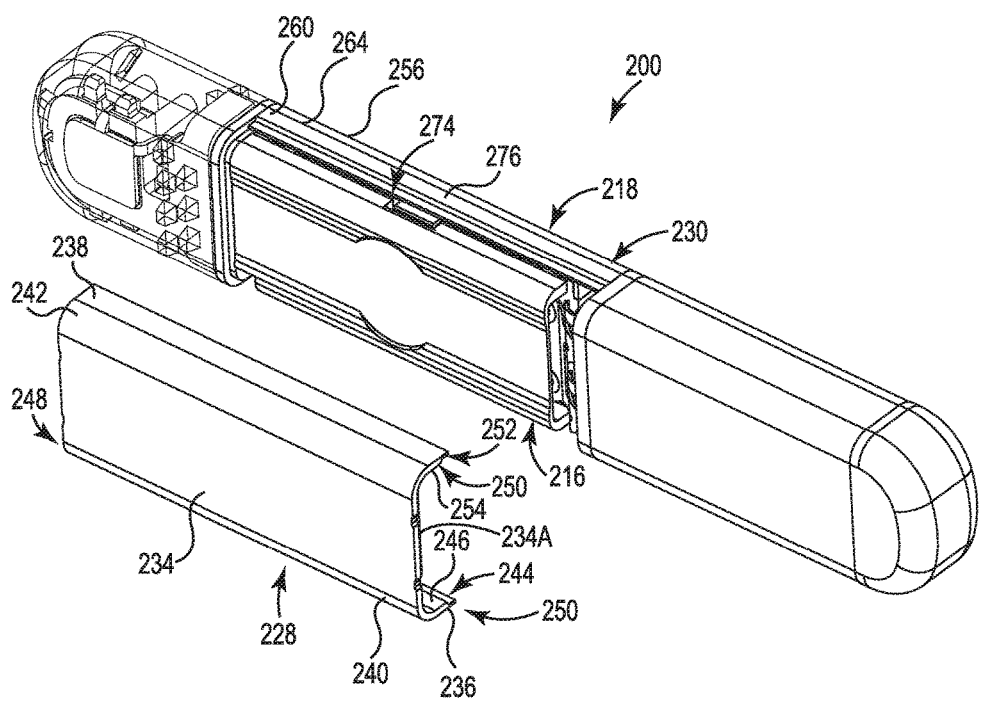
FIGS. 2B and 2C are partially-exploded perspective views of the IMD depicted in FIG. 2A, in accordance with embodiments of the disclosure.

As shown in FIG. 2B, the core assembly 204 includes a core circuitry assembly 216 enclosed within a core assembly housing 218. The core assembly housing 218 is coupled, at the first end 220, to a first feed-through assembly 222, and coupled, at the second end 224, to a second feed-through assembly 226. The feed-through assembly 222 may be configured to provide a throughput for connections configured to connect the circuitry components of the header 202 (e.g., the electrode 208 and the antenna 210) to the core circuitry assembly 216. Similarly, the feed-through assembly 226 may be configured to provide a throughput for connections configured to connect one or more batteries (e.g., which are a part of the battery assembly 206) and/or the electrode 214 to the core circuitry assembly 216.

As illustrated in FIG. 2A, the core assembly housing 204 includes a first portion 228 configured to be coupled to a second portion 230 along a weld seam 232. The first portion 228 and second portion 230 may be coupled together by laser welding, seam welding, and/or the like. In embodiments, a separate weld ring does not need to be used, as a feature of at least one of the first and second portions 228 and 230 acts as a weld ring, protecting the core circuitry assembly 216 from the welding energy (e.g., heat, laser, etc.).

For example, and as described in further detail below, the first portion 228 may include one or more weld joint features configured to be positioned adjacent to one or more corresponding weld joint features on the second portion 230 in preparation for welding. In embodiments, for example, the first portion 228 and the second portion 230 may include a continuous, curved wall (such as, for example, in an implementation of a pacemaker or other implantable pulse generator), a curved wall and a straight wall, a number of curved walls, a number of straight walls, and/or any number of different combinations of these. Each wall of the first portion 228 that is configured to be coupled to a corresponding wall of the second portion 230 may include at least one weld joint feature configured to be positioned adjacent to at least one corresponding feature on the second portion 230, and, in embodiments, vice-versa.

Each weld joint feature includes a thinned leading edge (the edge that is configured to be coupled to the corresponding edge of the other portion of the housing) of a wall. That is, the edge of the wall is thinner than other sections of the wall. In this manner, an edge of one of the two portions can pass over the corresponding edge of the other portion when the two portions are positioned around the core circuitry assembly in preparation for welding. In this manner, the volume enclosed within the housing may be maximized, and the lower edge (i.e., the edge closer to the core circuitry assembly) acts as a weld ring, protecting the core circuitry assembly from the applied energy (e.g., heat, laser, etc.) during a welding procedure. In embodiments, the weld joint feature may include a coined edge of a wall, a flange, and/or the like.

Figure 2C:
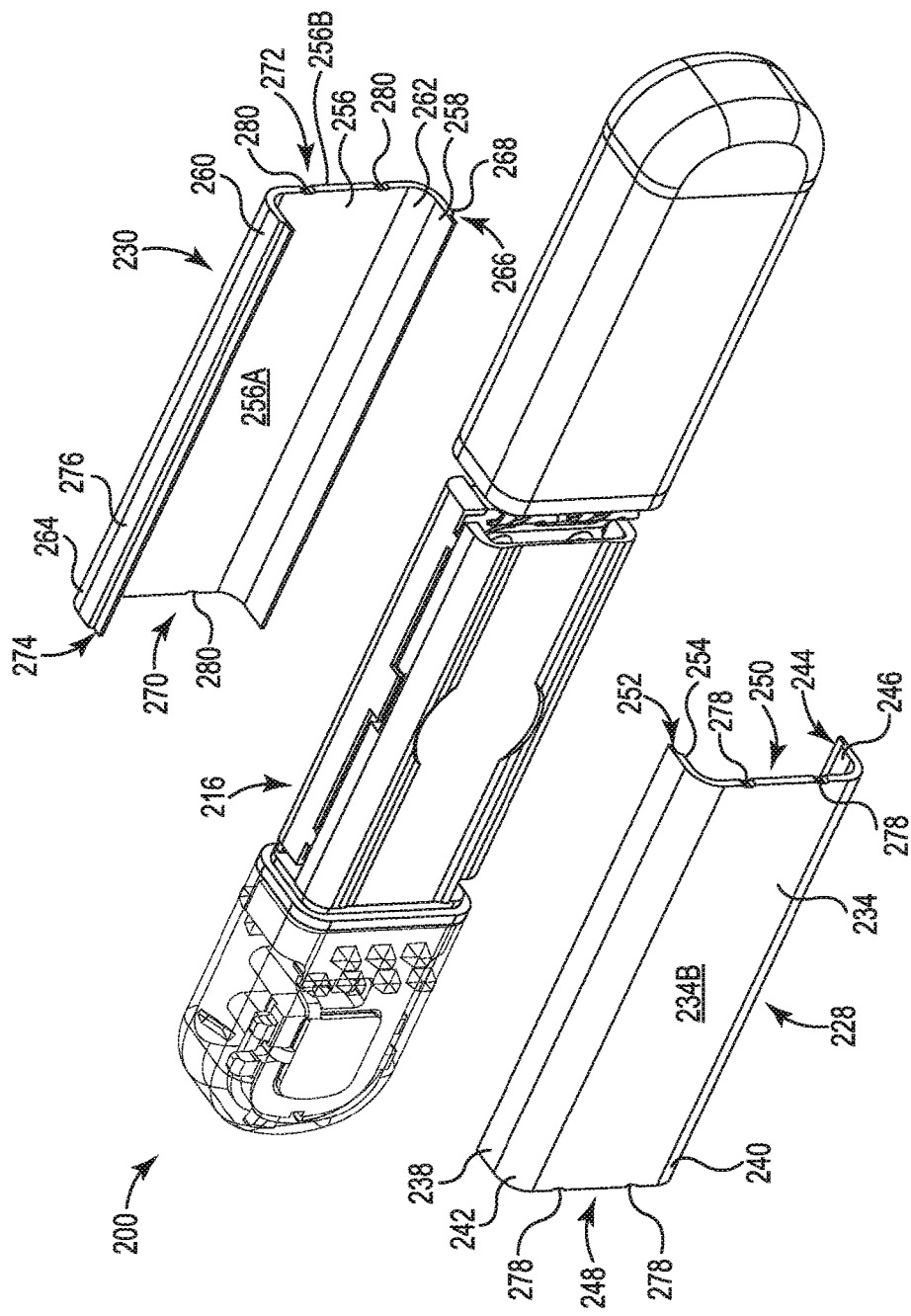

As shown, for example, in FIGS. 2B and 2C, the first portion 228 of the core assembly housing 218 includes a side wall 234, a lower wall 236, and an upper wall 238. The lower wall 236 and the upper wall 238 each extend, perpendicularly (or at least approximately perpendicularly) in a direction away from an inside surface 234A of the side wall 234. As shown, the lower wall 236 is coupled to the side wall 234 by a curved corner portion 240, and the upper wall 238 is coupled to the side wall 234 by a curved corner portion 242. In embodiments, the curved corner portions 240 and 242 may be integrated with the lower and upper walls 236 and 238, respectively, the side wall 234, and/or the like. That is, for example, the first portion 228 may be a single piece of metal, formed in a press or a mold. In embodiments, the curved corner portions 240 and 242 may be separate components. The curved corner portions 240 and 242 each may be designed to have any desirable radius of curvature. For example, the curved corner portions 240 and 242 each may be configured to have a radius of curvature that provides a desired amount of volume enclosed within the core assembly housing 218.

As illustrated, for example, in FIGS. 2B and 2C, the lower wall 236 includes a flange 244 that is recessed with respect to an inside surface 246 of the lower wall 236, and that extends from a first end 248 of the first portion 228 to a second end 250 thereof. The flange 244 may be a thinned portion of the lower wall 236. In embodiments, the flange 244 may be welded to the lower wall 236. Similarly, the upper wall 238 includes a flange 252 that is recessed with respect to an inside surface 254 of the upper wall 238, and that extends from the first end 248 of the first portion 228 to the second end 250 thereof. The flange 252 may be a thinned portion of the upper wall 238. In embodiments, the flange 252 may be welded to the upper wall 238.

As is also shown, for example, in FIGS. 2B and 2C, the second portion 230 of the core assembly housing 218 includes a side wall 256, a lower wall 258, and an upper wall 260. The lower wall 258 and the upper wall 260 each extend, perpendicularly (or at least approximately perpendicularly) in a direction away from an inside surface 256A of the side wall 256. As shown, the lower wall 258 is coupled to the side wall 256 by a curved corner portion 262, and the upper wall 260 is coupled to the side wall 256 by a curved corner portion 264. In embodiments, the curved corner portions 262 and 264 may be integrated with the lower and upper walls 258 and 260, respectively, the side wall 256, and/or the like. That is, for example, the second portion 230 may be a single piece of metal, formed in a press or a mold. In embodiments, the curved corner portions 262 and 264 may be separate components. The curved corner portions 262 and 264 each may be designed to have any desirable radius of curvature such as, for example, a radius of curvature that is identical or similar to the radius of curvature of each of the curved corner portions 240 and 242. For example, the curved corner portions 262 and 264 each may be configured to have a radius of curvature that provides a desired amount of volume enclosed within the core assembly housing 218.

As illustrated, for example, in FIGS. 2B and 2C, the lower wall 258 includes a flange 266 that is recessed with respect to an outside surface 268 of the lower wall 258, and that extends from a first end 270 of the second portion 230 to a second end 272 thereof. The flange 266 may be a thinned portion of the lower wall 258. In embodiments, the flange 266 may be welded to the lower wall 258. Similarly, the upper wall 260 includes a flange 274 that is recessed with respect to an outside surface 276 of the upper wall 260, and that extends from the first end 270 of the second portion 230 to the second end 272 thereof. The flange 274 may be a thinned portion of the upper wall 260. In embodiments, the flange 274 may be welded to the upper wall 260.

The core assembly housing 218 may also include notches 278 defined in the first and second ends 248 and 250, respectively, of the first portion 228, and extending from the inside surface 234A to the outside surface 234B of the side wall 234. Similarly, the core assembly housing 218 may also include notches 280 defined in the first and second ends 270 and 272, respectively, of the second portion 230, and extending from the inside surface 256A to the outside surface 256B of the side wall 256. The notches 278 and 280 may be an artifact of a progressive die manufacturing process in which the first and second portions 228 and 230 of the core assembly housing 218 are produced in a continuous strip and formed into shape in successive operations.

The notches 278 and 280 may be left when the first and second portions 228 and 230 are broken away from the strip. In embodiments, the strip may be configured such that the notches are small enough to be consumed in the weld pool when the core assembly housing 218 is welded to the first and second feedthrough assemblies 222 and 226. For example, in embodiments, the notches 278 and 280 may extend into the portions 228 and 230 by less than or equal to approximately 0.003 inches.

Figure 3A:
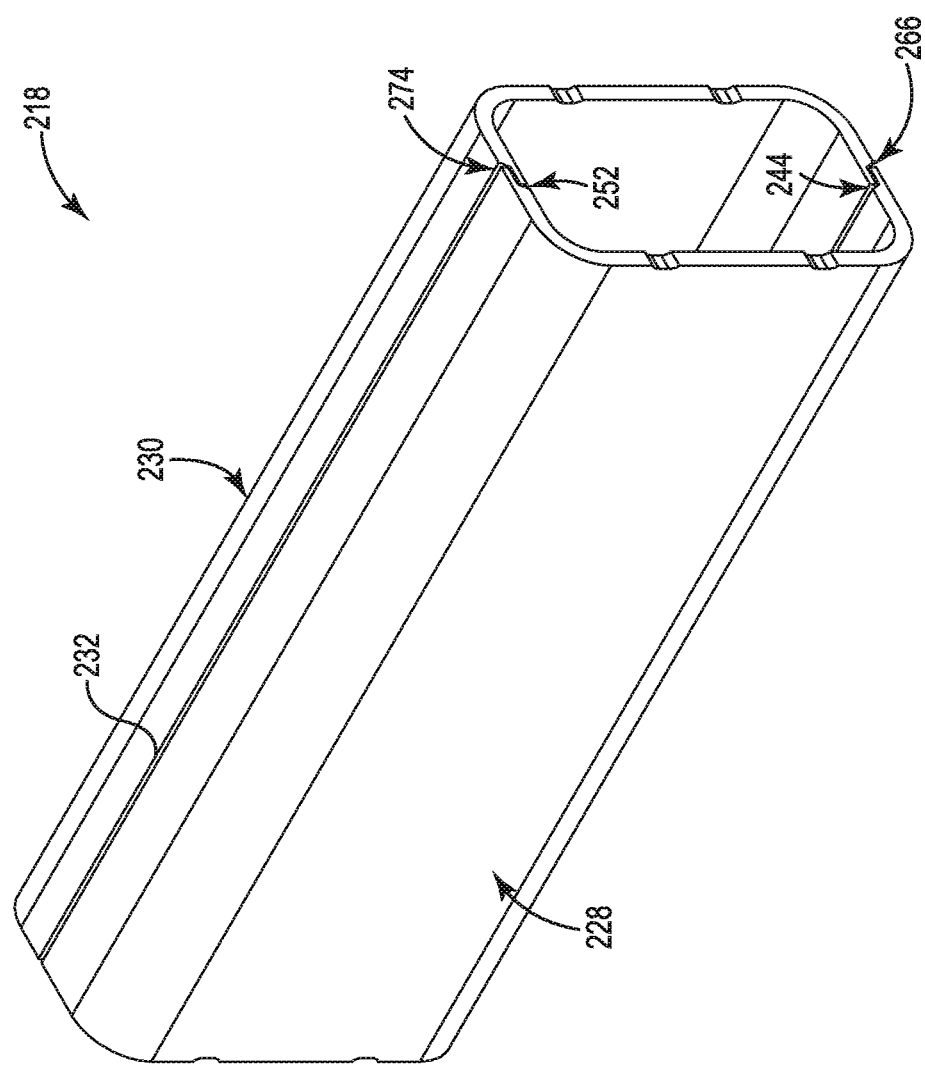
FIG. 3A is a perspective view of the core assembly housing of the IMD depicted in FIGS. 2A-2C, in accordance with embodiments of the disclosure.

As shown in FIG. 3A, when the first portion 228 is brought together with the second portion 230, the flange 244 is positioned adjacent to the flange 266, and the flange 252 is positioned adjacent to the flange 274. The portions 228 and 230 are welded together along the flanges 244, 266 and 252, 274 without the necessity of inserting a separate weld ring, since the flange 266 and flange 274 protect the core circuitry assembly 216, each flange 266 and 274 acting as an integrated weld ring.

Figure 3C:
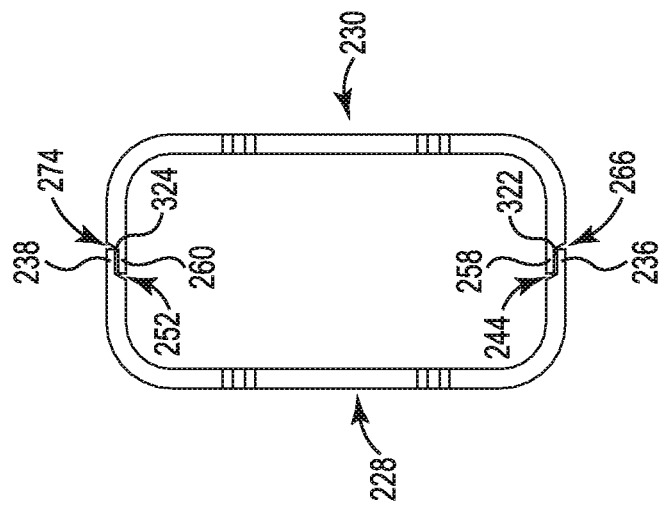
FIG. 3C is an assembled front view of the core assembly housing depicted in FIGS. 3A and 3B, in accordance with embodiments of the disclosure.
Figure 3B:
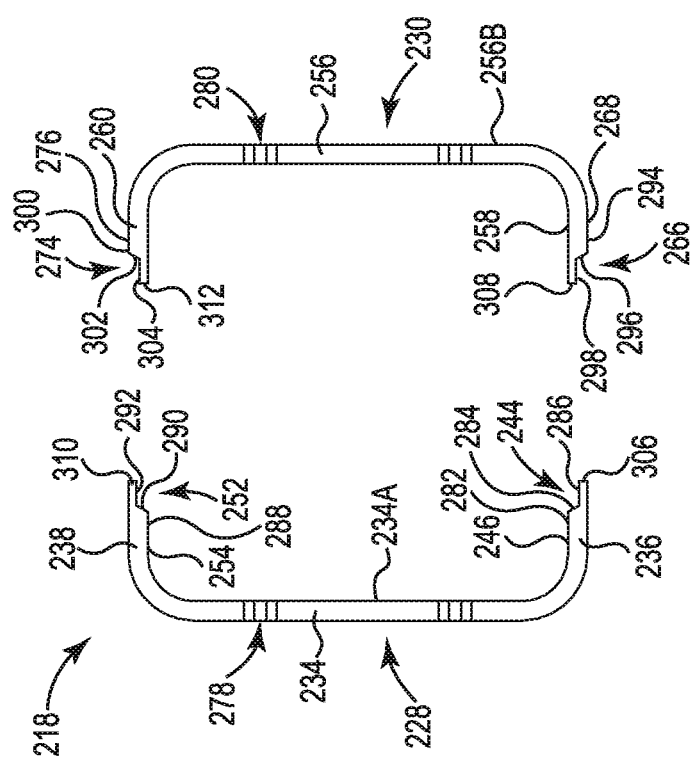
FIG. 3B is an exploded front view of the core assembly housing depicted in FIG. 3A, in accordance with embodiments of the disclosure.

As shown in FIGS. 3B and 3C, the flange 244 may be configured such that a first section 282 of the inside surface 246 of the lower wall 236 of the first portion 228 of the core assembly housing 218 is at least approximately continuous with the inside surface 234A of the side wall 234. A second section 284 of the inside surface 246 of the lower wall 236 may be oriented at an angle with respect to the first section 282 and may extend from an outside boundary of the first section 282 downward to a third section 286 of the inside surface 246. The third section 286 of the inside surface 246 may be oriented parallel to, or at least approximately parallel to, the first section 282. Thus, the second section 284 may be configured as a ramp extending between the first and third sections 282 and 286.

Similarly, the flange 252 may be configured such that a first section 288 of the inside surface 254 of the upper wall 238 of the first portion 228 of the core assembly housing 218 is at least approximately continuous with the inside surface 234A of the side wall 234. A second section 290 of the inside surface 254 of the upper wall 238 may be oriented at an angle with respect to the first section 288 and may extend from an outside boundary of the first section 288 upward to a third section 292 of the inside surface 254. The third section 292 of the inside surface 254 may be oriented parallel to, or at least approximately parallel to, the first section 288. Thus, the second section 290 may be configured as a ramp extending between the first and third sections 288 and 292.

In a similar manner, the flange 266 may be configured such that a first section 294 of the outside surface 268 of the lower wall 258 of the second portion 230 of the core assembly housing 218 is at least approximately continuous with the outside surface 256B of the side wall 256. A second section 296 of the outside surface 268 of the lower wall 258 may be oriented at an angle with respect to the first section 294 and may extend from the first section 294 upward to a third section 298 of the outside surface 268. The third section 298 of the outside surface 268 may be oriented parallel to, or at least approximately parallel to, the first section 294. Thus, the second section 296 may be configured as a ramp extending between the first and third sections 294 and 298.

Additionally, the flange 274 may be configured such that a first section 300 of the outside surface 276 of the upper wall 260 of the second portion 230 of the core assembly housing 218 is at least approximately continuous with the outside surface 256B of the side wall 256. A second section 302 of the outside surface 276 of the upper wall 260 may be oriented at an angle with respect to the first section 300 and may extend from the first section 300 downward to a third section 304 of the outside surface 276. The third section 304 of the outside surface 376 may be oriented parallel to, or at least approximately parallel to, the first section 300. Thus, the second section 302 may be configured as a ramp extending between the first and third sections 300 and 304.

During assembly, as shown in FIGS. 3B and 3C, when the first portion 228 and second portion 230 are brought together, a leading edge 306 of the lower wall 236 of the first portion 228 may be configured to be positioned adjacent to the second section 296 of the outside surface 268 of the lower wall 258 of the second portion 230, and a leading edge 308 of the lower wall 258 of the second portion 230 may be configured to be positioned adjacent to the second section 284 of the inside surface 246 of the lower wall 236 of the first portion 228, forming a gap 322. Similarly, a leading edge 310 of the upper wall 238 of the first portion 228 may be configured to be positioned adjacent to the second section 302 of the outside surface 276 of the upper wall 260 of the second portion 230, and a leading edge 312 of the upper wall 260 of the second portion 230 may be configured to be positioned adjacent to the second section 290 of the inside surface 254 of the upper wall 238 of the first portion 228, forming a gap 324. In this manner, the third sections 286, 292, 298, and 304 may be the weld surfaces, with the third sections 298 and 304 functioning as a weld ring, thereby protecting the core circuitry assembly 216 from the laser, heat, and/or other welding energy.

The illustrative IMD 200 shown in FIGS. 2A-2C and the illustrative core assembly housing 218 shown in FIGS. 3A-3C is not intended to suggest any limitation as to the scope of use or functionality of embodiments of the subject matter disclosed throughout this disclosure. Neither should the illustrative IMD 200 or illustrative core assembly housing 218 be interpreted as having any dependency or requirement related to any single component, feature, or combination of components or features illustrated in FIG. 2A-2C or 3A-3C. For example, in embodiments, the illustrative IMD 200 and/or illustrative core assembly housing 218 may include different and/or additional components and/or features. Any number of other components, features, or combinations of components or features can be integrated with the illustrative IMD 200 depicted in FIGS. 2A-2C and/or illustrative core assembly housing 218 depicted in FIGS. 3A-3C, all of which are considered to be within the ambit of this disclosure.

Additionally, any one or more of the components and/or features depicted in FIGS. 2A-2C and 3A-3C can be, in embodiments, integrated with various ones of the other components and/or features depicted therein (and/or components and/or features not illustrated). For example, instead of the flanges 244, 252, 266, and 274, the weld joint features may be wedge-shaped edges. That is, for example, the second section 284 and the third section 286 of the inside surface of the lower wall 236 of the first portion 228 may be integrated and include an at least approximately continuous decrease in thickness from the outside boundary of the first section 282 to the leading edge 306. Similarly, the second section 290 and the third section 292 of the inside surface of the upper wall 238 of the first portion 228 may be integrated and include an at least approximately continuous decrease in thickness from the outside boundary of the first section 288 to the leading edge 310; the second section 296 and the third section 298 of the outside surface 268 of the lower wall 258 of the second portion 230 may be integrated and include an at least approximately continuous decrease in thickness from the outside boundary of the first section 294 to the leading edge 308; and the second section 302 and the third section 304 of the outside surface 276 of the upper wall 260 of the second portion 230 may be integrated and include an at least approximately continuous decrease in thickness from the outside boundary of the first section 300 to the leading edge 312.

Additionally, in some embodiments, the core assembly housing 218 may include weld joint feature or features on only one portion. That is, for example, embodiments of the core assembly housing 218 may include only the flange 266 (or a wedge-shaped edge) and flange 274 (or a wedge-shaped edge) on the second portion 230, in which case the flanges 266 and 274 (or wedge-shaped edges) may include a surface extending farther inward (toward the core circuitry assembly) than the inside surfaces of the lower and upper walls 258 and 260, respectively.

Moreover, as used herein, the terms "side wall," "lower wall," "upper wall," "upward," and "downward" are used to refer to the specific features to which they refer, but are characterized in the context of the illustrations for clarity and to describe relative orientations of features with respect to other features, and are not intended to imply any particular orientation of the IMD 200, or absolute (or preferred) orientations of features thereof. That is, for example, even if the IMD 200 were to be rotated around a longitudinal axis such that the outer surface 234B of the side wall 234 was parallel to a horizontal plane, the side wall 234 would still be referred to, for the purposes of this disclosure, as a "side wall."

Figure 4:
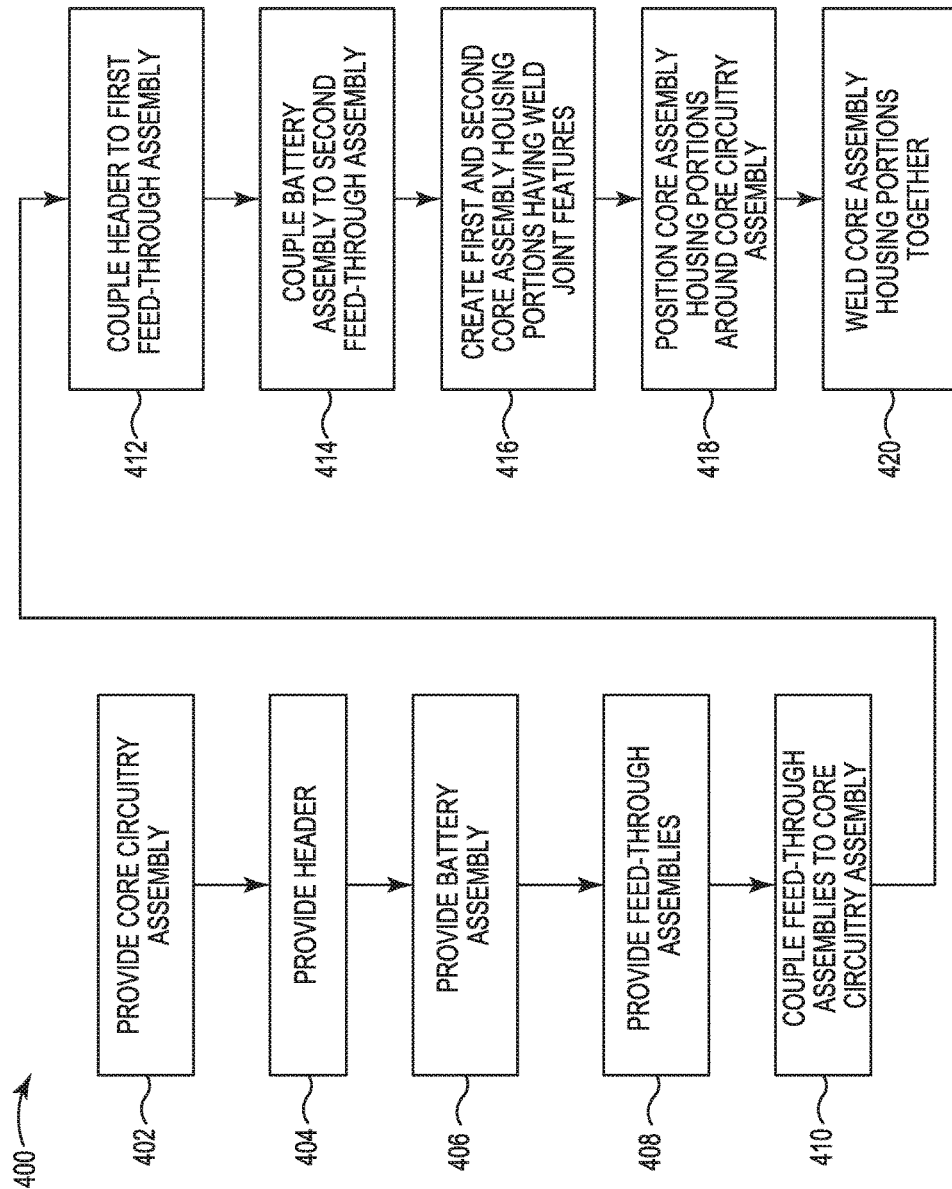
FIG. 4 is a flowchart depicting an illustrative method of assembling an IMD, in accordance with embodiments of the disclosure.

Embodiments of an IMD having a core assembly housing configured to be assembled without the use of a weld ring are described above, and include configurations designed to enhance the internal volume of the IMD. FIG. 4 is a flow diagram depicting an illustrative method 400 of manufacturing an IMD in accordance with embodiments of the disclosure. The IMD may be, for example, the IMD 102 depicted in FIG. 1, the IMD 200 depicted in FIGS. 2A-2C, and/or the like.

Embodiments of the method 400 include providing a core circuitry assembly (block 402), which may include obtaining and/or assembling one or more portions of a core circuitry assembly such as, for example, by assembling an integrated circuit, coupling circuitry to a liner, and/or the like. The method 400 also may include providing a header (block 404), which may include obtaining and/or assembling one or more portions of a header such as, for example, by arranging circuit components (e.g., an electrode and an antenna) on a scaffold assembly and enclosing the scaffold assembly within a header assembly housing. The method 400 may also include providing a battery assembly (block 406) and providing feed-through assemblies (block 408), which may include obtaining and/or assembling a battery assembly and/or a first and second feed-through assembly.

As depicted in FIG. 4, embodiments of the method 400 also include coupling the feed-through assemblies to the core circuitry assembly (block 410), coupling the header to a first feed-through assembly (block 412), and coupling the battery assembly to a second feed-through assembly (block 414). In embodiments, the method 400 includes creating first and second portions of a core assembly housing, having weld joint features (block 416). In embodiments, the core assembly housing portions may be molded, cut, and/or the like, and may be identical or similar to the core assembly housing portions 228 and 230 depicted in FIGS. 2A-2C and 3A-3C. As shown in FIG. 4, embodiments of the method 400 also include positioning the core assembly housing portions around the core circuitry assembly (block 418) and welding the core assembly housing portions together along the weld joint features (block 420).

Various modifications and additions can be made to the exemplary embodiments discussed without departing from the scope of the disclosed subject matter. For example, while the embodiments described above refer to particular features, the scope of this disclosure also includes embodiments having different combinations of features and embodiments that do not include all of the described features. Accordingly, the scope of the disclosed subject matter is intended to embrace all such alternatives, modifications, and variations as fall within the scope of the claims, together with all equivalents thereof.

We claim:

1. A medical device comprising:
   a core circuitry assembly; and
   a core assembly housing configured to enclose the core circuitry assembly, the core assembly housing comprising:
   a first portion comprising:
      a first side wall, the first side wall comprising a first end and a second end, wherein the first end comprises at least one notch and wherein the second end comprises at least one;
      a first lower wall coupled to the first wall by a first corner portion and extending in a direction away from an inside surface of the first side wall; and
      a first upper wall coupled to the first side wall by a second corner portion and extending in a direction away from the inside surface of the first side wall; and
   a second portion configured to be coupled to the first portion along a weld seam, the second portion comprising;
      a second side wall, the second side wall comprising a first end and a second end, wherein the first end comprises at least one notch and wherein the second end comprises at least one notch;
      a second lower wall coupled to the second side wall by a third corner portion and extending in a direction away from an inside surface of the second side wall;
      a second upper wall coupled to the side wall by a second corner portion and extending in a direction away from an inside surface of the second side wall; and
   at least one weld joint feature, wherein the at least one weld joint feature includes a wedged-shaped section of an outside surface of the second lower wall, a wedged-shape section of an outside surface of the second upper wall, a wedged-shaped section of an inside surface of the first lower wall, and a wedge-shaped section of an inside surface of the first upper wall.

2. The medical device of claim 1, wherein the at least one weld joint feature comprises at least one of a flange and a wedge-shaped edge of at least one wall of the second portion.

3. The medical device of claim 1, wherein the at least one weld joint feature includes a first flange that is recessed with respect to an outside surface of the second lower wall and a second flange that is recessed with respect to an outside surface of the second upper wall.

4. The medical device of claim 3, the at least one weld joint feature further comprising a third flange that is recessed with respect to an inside surface of the first lower wall and a fourth flange that is recessed with respect to an inside surface of the first upper wall.

5. The medical device of claim 3, wherein the first and second flanges act as an integrated weld ring to protect the core circuitry assembly from the energy applied during a welding procedure.

6. The medical device of claim 1, wherein the wedge-shaped section of the outside surface of the second lower wall and the wedge-shaped section of the outside surface of the second upper wall act as an integrated weld ring to protect the core circuitry assembly from the energy applied during a welding procedure.

7. A medical device comprising:
   a core circuitry assembly; and
   a core assembly housing configured to enclose the core circuitry assembly, the core assembly housing comprising:
   a first portion comprising: (1) a first side wall, the first side wall comprising a first end and a second end, wherein the first end comprises at least one notch and wherein the second end comprises at least one; (2) a first lower wall coupled to the first side wall by a first curved corner portion and extending in a direction away from an inside surface of the first side wall; and (3) a first upper wall coupled to the first side wall by a second curved corner portion and extending in a direction away from the inside surface of the first side wall;

a second portion configured to be coupled to the first portion along a weld seam, the second portion comprising: (1) a second side wall, the second side wall comprising a first end and a second end, wherein the first end comprises at least one notch and wherein the second end comprises at least one notch; (2) a second lower wall coupled to the second side wall by a third curved corner portion and extending in a direction away from an inside surface of the second side wall; and (3) a second upper wall coupled to the side wall by a second curved corner portion and extending in a direction away from an inside surface of the second side wall; and at least one weld joint feature, wherein the at least one weld joint feature includes a wedged-shaped section of an outside surface of the second lower wall, a wedged-shape section of an outside surface of the second upper wall, a wedged-shaped section of an inside surface of the first lower wall, and a wedge-shaped section of an inside surface of the first upper wall.

8. The medical device of claim 7, the at least one weld joint feature includes a thinned section of the second portion that is recessed with respect to an outer surface of a wall of the second portion and a thinned section of the first portion that is recessed with respect to an inner surface of a wall of the first portion, wherein the thinned section of the second portion comprises a first flange that is recessed with respect to an outside surface of the second lower wall and a second flange that is recessed with respect to an outside surface of the second upper wall.

9. The medical device of claim 8, wherein the thinned section of the first portion comprises a third flange that is recessed with respect to an inside surface of the first lower wall and a fourth flange that is recessed with respect to an inside surface of the first upper wall.

10. The medical device of claim 8, wherein the first and second flanges act as an integrated weld ring to protect the core circuitry assembly from the energy applied during a welding procedure.

11. The medical device of claim 7, wherein the wedge-shaped section of the outside surface of the second lower wall and the wedge-shaped section of the outside surface of the second upper wall act as an integrated weld ring to protect the core circuitry assembly from the energy applied during a welding procedure.

* * * * *